United States Patent [19]

Davis, Jr.

[11] Patent Number: 5,626,583
[45] Date of Patent: May 6, 1997

[54] PROXIMAL MANDIBULAR SEGMENT POSITIONER

[76] Inventor: Wilbur M. Davis, Jr., 610 North Mills Ave., Orlando, Fla. 32803

[21] Appl. No.: 426,823

[22] Filed: Apr. 21, 1995

[51] Int. Cl.$^6$ .......................................... A61B 17/56
[52] U.S. Cl. .......................... 606/72; 128/777; 128/898
[58] Field of Search ..................... 433/141, 72, 75, 433/229, 215, 143, 145, 144; 128/776, 777, 898

[56] References Cited

U.S. PATENT DOCUMENTS

| | | |
|---|---|---|
| 214,923 | 4/1879 | Justi . |
| 550,508 | 11/1895 | How . |
| 1,586,302 | 5/1926 | Funk . |
| 1,818,627 | 8/1931 | Kerr .................... 433/72 |
| 3,559,292 | 2/1971 | Weissman ............... 433/72 |
| 4,552,531 | 11/1985 | Martin . |
| 4,759,713 | 7/1988 | Heiss et al. . |
| 4,768,952 | 9/1988 | Loewenthal . |
| 4,800,873 | 1/1989 | Audell . |
| 4,979,898 | 12/1990 | Rand .................... 433/72 |
| 5,022,859 | 6/1991 | Oliva . |
| 5,098,292 | 3/1992 | Lazarof . |
| 5,161,971 | 11/1992 | Neiner et al. . |

Primary Examiner—Michael Buiz
Assistant Examiner—Kevin Truong
Attorney, Agent, or Firm—Quarles & Brady

[57] ABSTRACT

A method and instrument for positioning a proximal segment of a buccal cortex to seat a condyle in the fossa during TMJ corrective procedures includes osteotomizing a mandible, thereby forming a proximal segment and a distal segment, drilling a burr hole in the proximal segment adjacent the osteotomy and inserting, into the hole, the tip of a positioning instrument having a handle, an elongated shaft and a stepped down tip angled approximately 45° relative to the axis of the handle and shaft. The instrument can be manipulated from the patient's mouth in a minimally invasive and secure fashion.

15 Claims, 2 Drawing Sheets

PROXIMAL MANDIBULAR SEGMENT POSITIONER

FIELD OF THE INVENTION

The invention relates generally to a technique and instrument for positioning an osteotomized mandibular bone segment during an orthognathic surgical procedure. More specifically, the invention relates to a method and instrument for the surgical positioning of the proximal mandibular bone segment in the SSRO (sagittal split ramus osteotomy) orthognathic procedure to assist in the correct anatomical positioning of the mandibular condyle in the glenoid fossa.

BACKGROUND OF THE INVENTION

A commonly performed orthognathic surgical procedure is the SSRO (sagittal split ramus osteotomy). This procedure is typically performed on patients with a malocclusion or condition in which the lower teeth of the mandible do not line up with the upper teeth of the maxilla. These conditions are most commonly manifest in what are known as an "overbite" or an "underbite."

The SSRO surgical procedure involves performing osteotomies or bone cuts in a specific pattern in the buccal (towards the cheek) and lingual (towards the tongue) cortical plates of the mandible such that the cortical plates are split and the mandible is divided into two proximal segments bilaterally and a distal segment centrally. The distal or tooth bearing fragment is thus freed from the proximal, condylar bearing fragments, which form the joints with the base of the skull, such that the distal fragment can be positioned into the correct occlusal relationship with the teeth of the maxilla.

The teeth of the distal fragment, and hence the distal fragment itself, are typically fixed by wires to the teeth of the maxilla during the surgical procedure to establish its correct positioning. Once this has been accomplished, the surgeon is faced with the task of repositioning the free proximal segments prior to application of fixation hardware to reunite the proximal and distal fragments for bone healing in their new relative positions.

The most important consideration in repositioning the proximal segments prior to application of the fixation hardware is to insure that the condylar part of the proximal segment is correctly seated in the glenoid fossa of the base of the skull. This is of critical importance for a number of reasons. If the condyle is not correctly seated into the glenoid fossa at the time of application of the fixation hardware a malocclusion will occur post-operatively. This malocclusion can be caused by the pull of muscles attached to the mandible that will work to reseat the condyle into the fossa to create a functional joint condition. Since the distal segment has been reattached to the proximal segments via the fixation hardware and later by healing of the bone, the condyles migration back into the fossa will move the mandibular teeth back into a condition of malocclusion, negating the whole intent of the surgery in the first place.

There is also the possibility that if the condyle is not correctly positioned and seated in the fossa at the time of surgery, it may not become fully reseated in the fossa by muscle forces post-surgically.

Surgeons have recognized the importance of correctly positioning the condyle in the fossa during the SSRO procedure and have developed a number of techniques and appliances to accomplish this seating. The appliances have traditionally taken the form of a bone fixation plate that is attached to the maxilla and the proximal segment prior to separation of the proximal and distal mandibular segments.

The intent of these devices is to maintain the position of the proximal segment relative to the fossa throughout the surgical procedure and application of fixation hardware. Once the fixation hardware is applied, the positioning appliance can be removed.

A key problem with this approach involves the fact that the patient is under anesthesia prior to application of these appliances. Because of a lack of muscle tonus during anesthesia, the condyle "falls" out of the fossa and is therefore not in fact correctly positioned at all.

Another common technique for seating of the condyle involves the use of a gauze packer instrument. The gauze packer is an instrument with a coaxial handle and shaft with a bifurcated or forked end. After splitting the proximal segments from the distal segment, the surgeon uses a rotating cutting burr to create a notch in the front edge of the proximal segment. The surgeon then uses the gauze packer instrument by placing its forked end into the notch and directing a force via the instrument into the proximal segment posteriorly and inferiorly while at the same time lifting up externally at the angle of the mandible with digital pressure. The resultant forces applied to the proximal segment serve to push the condyle upwards and forward into the fossa to effect the seating of the condyle. This technique is known as the bi-vector condylar seating technique. The fixation hardware is then applied to fix the segments in their new relative positions.

This instrument has the drawback of only allowing the surgeon to apply forces to the proximal segment in basically one direction. This is particularly disadvantageous at the beginning of the condylar seating process when the surgeon may wish to manipulate the proximal segment in a number of different directions and planes to get the segment settled into an appropriate position relative to the soft tissues and the distal segment prior to final seating.

SUMMARY OF THE INVENTION

It is an object of the invention to provide a method and instrument to facilitate the positioning of a proximal mandibular segment to accurately and reliably position the condyle into the fossa.

It is another object of the invention to provide a method and instrument that readily permits mandibular segment movements from different directions and angles without compromising the integrity of the engagement of the instrument to the segment.

It is a further object of the invention to provide an instrument for proximal mandibular segment positioning that retards over-insertion into the mounting hole and provides positive, tactile indication of proper instrument insertion.

These and other objects of the invention are provided by an instrument that offers an improved method of accomplishing the bi-vector condylar seating technique. The subject instrument provides a means of controlling the positioning and seating of the proximal segment and the condyle by engaging the instrument into a hole created in the buccal cortex of the proximal segment. The hole can be created by a rotating cutting burr commonly available in the operating room.

The instrument preferably includes a handle for grasping by a surgeon's hand, a coaxially positioned smaller diameter shaft of sufficient length to reach from the extraorally positioned handle to the area of the osteotomy in the mandible, a bend of approximately 45° near the end of the shaft to provide for efficient access transorally and proper direction of force, and a reduced diameter tip sized to engage a burr hole created in the buccal cortex while at the same time allowing for a stop formed, for example, by the larger diameter shaft that will sit against the surface of the buccal cortex. The reduced diameter tip can also have a chamfered end to increase the ease of engagement of the reduced diameter tip into the burr hole. The reduced diameter tip could also be substituted for a conical or fully radiused tip so long as these other tips have a maximum diameter less than a transverse face, defined either by the shaft diameter or an extension, so that a stop is provided to contact the surface of the buccal cortex.

According to one version of the method of the invention, a patient's mandible osteotomized into a proximal segment and a distal segment, and a hole is positioned to intersect the proximal segment; and an instrument constructed according to the invention is inserted to manipulate the segment to position the condyle in the fossa.

As described above, said instrument has a shaft transitioning to a tip. Although the tip is preferably circular in cross section, the tip and shaft could have other cross-sectional geometries.

Unless the tip has a stop-limiting periphery, it should have a smaller peripheral width than a peripheral width of a transverse face associated the shaft. In one method of the invention, the insertion of the instrument into the segment is limited by an engagement of the peripheral width of the tip and the burr hole, and the instrument is manipulated to seat the condyle in the fossa. In another version of the method of the invention, the insertion is limited by abutment of the transverse face between the tip and the rest of the shaft with the proximal segment.

Other objects and advantages of the present invention will be apparent from the description below. However, this description is only of the preferred embodiments. The claims should, therefore, be looked to in order to assess the whole scope of the invention.

BRIEF DESCRIPTION OF THE DRAWINGS

A more detailed understanding of the invention can be gained from a reading of the following detailed description in connection with the associated drawings, in which.

DETAILED DESCRIPTION OF THE EMBODIMENTS OF THE INVENTION

Figure 1:
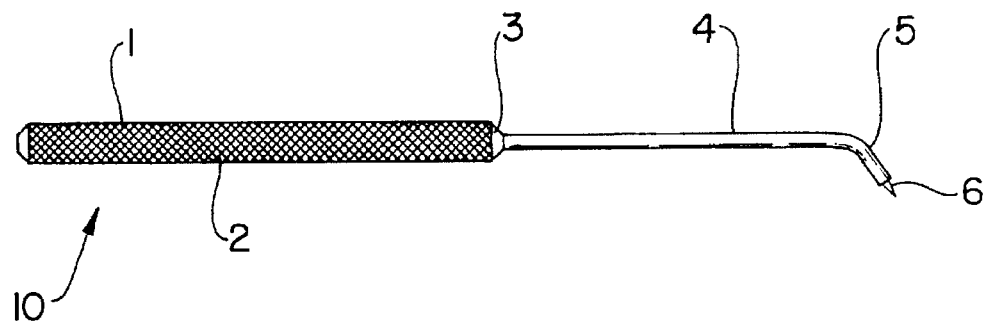
FIG. 1 is a plan view of an embodiment of the instrument of the present invention.

The invention is directed to an instrument and method for accurately and reliably positioning an osteotomized proximal mandibular segment to seat its condylar part in the glenoid fossa. FIG. 1 shows a plan view of one embodiment of the instrument of the present invention. The instrument is adapted for positioning the proximal segment of an osteotomized mandible to seat the mandibular condyle in a fossa. The instrument provides a tip for insertion into a burr hole preferably drilled through a proximal segment of the osteotomized mandible. The hole may be drilled, cut or otherwise formed, using a drill, a rotating burr or similar tool. The hole preferably has a circular geometry but need not be limited to this shape.

A first handle portion 1 of the instrument 10 is adapted for grasping by the human hand. It may be a substantially cylindrical piece having a textured surface 2 designed for ease of grasping and prevention of slipping. The handle may be formed in other shapes so long as it is reliably grippable for maneuvering during the procedure of the invention.

A second, preferably substantially cylindrical shaft portion 4 is attached coaxially to the first handle portion 1. Typically, the second shaft portion 4 will be of a smaller diameter than the first handle portion 1. Thus, a bevel 3 can transition the reduction in diameter from the first handle portion 1 to the second shaft portion 4. While a circular cross section for the shaft portion 4 is preferred, a variety of polygonal shapes are considered to be within the scope of the invention.

Figure 5:
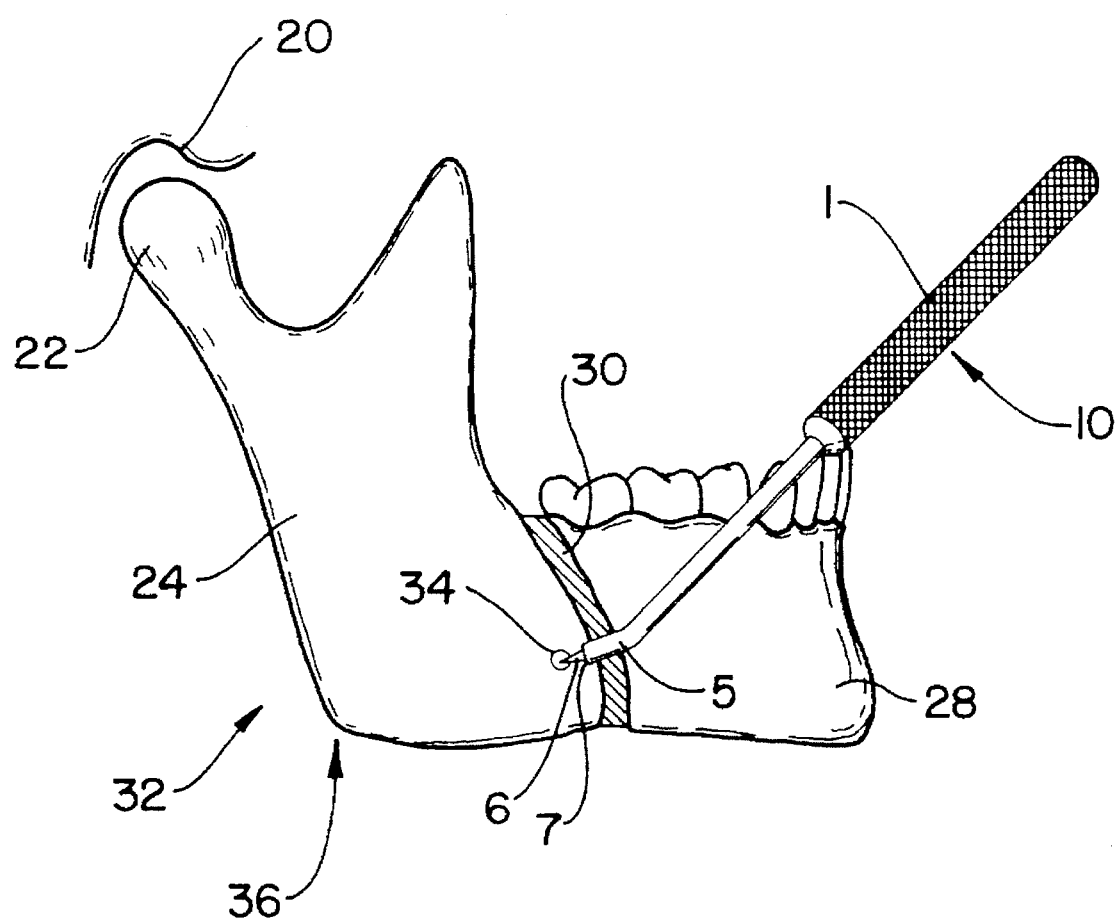
FIG. 5 is a schematic of one embodiment of the method of the present invention.

A third preferably substantially cylindrical shaft portion 5 is attached coaxially to the second shaft portion 4 and is preferably sized to engage a periphery of a hole drilled in the mandibular segment (See FIG. 5). Again, this shaft portion 5 may also have a polygonal cross section. The third shaft portion 5 preferably has about a 45° radial bend in relation to the axis of the first handle portion 1 and the second shaft portion 4.

A tip 6 is formed at the end of the third shaft portion 5 and is sized to at least partially insert and engage the mandibular burr hole. The tip 6 serves to securely engage the instrument 10 with the mandibular segment to be positioned and, in conjunction with the shaft portion 5, limits the depth of insertion to prevent potential impinging on the underlying mandibular nerve. The limited insertion and positive engagement also assist in accurately conveying the positioning maneuvers of the user to a corresponding movement of the mandibular segment, without error due to slippage or over-insertion. The tip can be constructed in a variety of geometries to accomplish these objectives.

It is preferred that the tip 6 provides a diameter (or periphery in non-circular constructions) that is either large enough to engage the burr hole or is less than the diameter of a transverse face define by the shaft portion 5 or an extension thereof so that along the transition from the smaller diameter on the tip 6 to the transverse face, the edge of the burr hole in the mandibular segment is engaged and insertion is limited. As it is possible that the tip 6 and the shaft 5 may alternatively have non-circular, polygonal cross sections, for example, octagonal, it is correspondingly preferred that the peripheral width, which refers to the longest extension across the polygonal cross section, of the tip 6 is less than the peripheral width of the transverse face if a transverse face is used to limit insertion. Of course, in the case of the preferred circular cross section, the peripheral width refers to the diameter.

Figure 2:
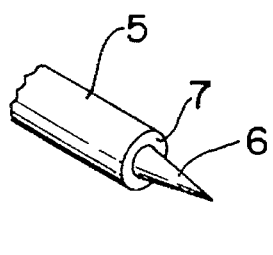
FIG. 2 is a perspective view of one tip embodiment for the instrument of the invention.

Among the various constructions possible for the tip 6 within the scope of the invention, a few are preferred. Referring to FIG. 2, the tip 6 can provide a conical taper from the larger diameter of the third shaft portion 5, which is illustrated as broken away from the remainder of the instrument 10. Preferably, the tip 6 can have a stepped reduced diameter such that an annular face 7 is formed at the junction of the tip 6 and the remainder of the third shaft portion 5.

The annular face 7 provides a stop abutment for positive engagement with the hole in the mandibular segment to be positioned and limits the insertion of the instrument into the hole. As discussed above, this insertion limit prevents overpenetration not only during insertion but also during positioning manipulation of the proximal segment, which likely involves forces in the insertion direction.

The limiting tip 6 also provides a positive tactile indication that insertion has occurred. Similarly, during manipulation of the segment to seat the condyle, the positive engagement combined with the angled shaft portion enhance the accuracy of the response of the segment motion to the manipulation forces because slippage and over-insertion are minimized or eliminated.

Figure 3:
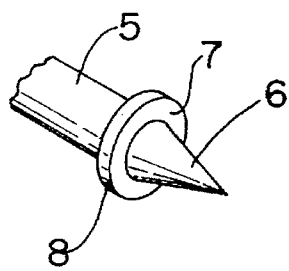
FIG. 3 is a perspective view of another tip embodiment for the instrument of the invention.

Referring to FIG. 3, the tip 6 can conically taper. In this embodiment, the tip 6 inserts into the hole drilled in the mandibular segment until it matches the diameter of the hole, which is preferably smaller than the full diameter of the third shaft portion 5 beyond the taper. FIG. 3 also illustrates the possibility of an extension, such as a collar 8, to provide a transverse face 7 for limiting engagement. Also, the extension can be provided by a bar or other structure that can provide a transverse engagement face. In this construction, the tip 6 could have a diameter as large as or larger than the shaft 5. Alternatively, the transverse face could be provided by other constructions, such as a groove in the tip or shaft that is inserted and laterally shifted into engagement with the edge of the burr hole.

Figure 4:
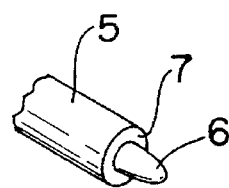
FIG. 4 is a perspective view of another tip embodiment for the instrument of the invention.

Referring to FIG. 4, the tip 6 can provide a cylindrical contour with a rounded end or chamfer. As illustrated, the stepped reduction in diameter can be used to provide a limiting annular transverse face 7.

Each portion of the instrument may be made of a solid or hollow material. Preferably, the material is a metal, with the metal preferably being stainless steel. Alternatively, the instrument can be constructed with plastic, anodized aluminum or titanium.

Preferably, the instrument is constructed out of a single piece of material. Alternatively, the various portions can be fused together. Typically, the instrument will be reused after being sterilized, but the instrument can also be made of a disposal material.

In a preferred embodiment, the entire instrument is about 7 inches long with a 4 inch handle and a 3 inch shaft and tip. The tip is preferably angled at 4°–55°, but can range from 30°–90°, with the third shaft portion and tip having a length of about ½ inch together and the tip itself being ⅕ inch.

Referring to FIG. 5, in operation, the patient's mandible 32 is osteotomized at cut 30 on the illustrated buccal plate and on the lingual plate (not shown), thereby forming a proximal segment 24 and a distal segment 28. A similar cut can be performed on the other half of the mandible to form a second proximal segment (not shown). A hole 34 is then drilled, cut or otherwise provided and positioned to engage the proximal segment 24. Typically, the hole 34 is started in the buccal cortex and can be placed anywhere adjacent the vertical osteotomy 30.

Drilling or cutting is the preferred means for forming the burr hole 34 and relates to another advantage of the invention. Because the mounting hole 34 is pre-drilled and the instrument 10 is inserted without puncture force that would be otherwise required, the lateral forces imparted on the mandible segment 24 are significantly reduced, thereby avoiding damage to the condylar region as well as damage to the soft tissue ligament and muscle attachments of the mandible.

The tip 6 of the instrument 10 is then inserted into the hole to thereby engage the tip 6, or the annular face 7, of the instrument with the proximal segment 24. The instrument 10 is then manipulated to seat the condyle 22 in the fossa 20.

The angling of the shaft end 5 and the tip 6 relative to the handle 1 permits a wide range of maneuvering motions from the external handle location. Because of the angled insertion, motions up and down, right and left and in and out can be performed without removal or slippage of the instrument tip 6 from the burr hole 34. The limiting engagement of the inventive tip 6 in combination with the angled shaft 5 enhance the integrity of the engagement and reliability of the mandible's accurate response to motions imparted through the handle of the instrument.

The angled bend and the transverse face adjacent to the tip provide the additional benefit of permitting movement of the proximal fragment in all planes of space. Manipulation of the proximal segment in this way allows the surgeon to perform a tactile inspection of the osteotomy and discover any significant irregularities that exist between the two bone surfaces that may cause limited contact between the bone segments and hence instability and compromised bone healing.

Once the surgeon discovers such bone surface irregularities by using the instrument to manipulate the proximal fragment relative to the distal fragment, the surgeon may go back and eliminate the irregularities with a bone rasp or rotating burr. The surgeon then proceeds with positioning of the proximal segment and seating of the condyle using the instrument.

With the tip 6 of the instrument 10 engaged in the burr hole 34 in the buccal cortex of the proximal segment, a force vector is imparted by the surgeon through the handle 1 such that an inferior (downward) and posterior (towards the back) force is imparted to the proximal segment in the area of the burr hole 34. At the same time, a second force vector is imparted by the surgeon using digital pressure at the inferior border of the mandible near the mandibular angle 36 in a superior (upward) direction. The resulting force vector at the condyle is in a superior and anterior (forward) direction that serves to seat the condyle in its correct anatomical position in the fossa.

While the surgeon applies these seating forces through the instrument 10 and digital pressure, an assisting surgeon can apply fixation hardware, such as bone screws and plates across the proximal and distal mandibular segments to provide post-operative stability to the fragments while the bone healing in the new relative position of the fragments occurs.

The angled bend and the transverse face adjacent to the tip provide the additional benefit of permitting movement of the proximal fragment in all planes of space. Manipulation of the proximal segment in this way allows the surgeon to perform a tactile inspection and discover any significant irregularities that exist between the two bone surfaces that may cause limited contact between the bone segments and hence instability and compromised bone healing. Once the surgeon discovers such bone surface irregularities by using the instrument to manipulate the proximal fragment relative to the distal fragment, the surgeon may go back and eliminate the irregularities with a bone rasp or rotating burr. The surgeon then proceeds with positioning of the proximal segment and seating of the condyle using the instrument.

The foregoing description is primarily directed to preferred embodiment of the instrument and method of the invention even though reference to various alternatives have been made. Further variations to the invention may now be apparent to one skilled in the relevant field. Accordingly, the scope of the invention should not be assessed by the description but rather should be based on a reading of the following claims.

I claim:

1. A method of seating a condyle of a proximal mandibular segment in a fossa, said method comprising the steps of:

osteotomizing a patient's mandible into at least one proximal segment and a distal segment;

providing a hole in the proximal segment;

inserting a tip of an elongated instrument into the hole, said instrument having a handle and a shaft transitioning to the tip, said tip having a smaller peripheral width than a peripheral width of the shaft, said tip being angled relative to an axis of said handle;

limiting the tip insertion by an engagement of a peripheral width of the tip and the hole; and manipulating the instrument by the handle to seat the condyle in the fossa.

2. The method according to claim 1, wherein the angle of the tip is approximately 45°.

3. The method according to claim 1, wherein the hole is provided by drilling.

4. The method according to claim 1, wherein the hole is provided by cutting with a rotating burr.

5. The method according to claim 1, wherein the tip is circular in cross section and said peripheral width is a diameter.

6. The method according to claim 5, wherein the tip is conical.

7. The method according to claim 5, wherein the tip is cylindrical and has a rounded end.

8. A method of seating a condyle of a proximal mandibular segment in a fossa, said method comprising the steps of:

osteotomizing a patient's mandible into at least one proximal segment and a distal segment;

providing a hole in the proximal segment;

inserting a tip of an elongated instrument into the hole, said instrument having a handle and a shaft transitioning to the tip, said tip being angled relative to an axis of said handle;

limiting the insertion by an engagement of a transverse face structure, connected to the shaft, with the segment; and manipulating the instrument by the handle to seat the condyle in the fossa.

9. The method according to claim 8, wherein said tip has a largest peripheral width that is smaller than a peripheral width of the transverse face.

10. The method according to claim 8, wherein the transverse face is provided by the shaft.

11. The method according to claim 8, wherein the transverse face is provided by an extension connected to the shaft.

12. The method according to claim 11, wherein the extension is a collar.

13. The method according to claim 8, wherein the angle of the tip is approximately 45°.

14. The method according to claim 8, wherein the hole is provided by drilling.

15. The method according to claim 8, wherein the hole is provided by cutting with a rotating burr.

* * * * *